United States Patent [19]

Harandi et al.

[11] Patent Number: 4,988,366
[45] Date of Patent: Jan. 29, 1991

[54] HIGH CONVERSION TAME AND MTBE PRODUCTION PROCESS

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 427,221

[22] Filed: Oct. 24, 1989

[51] Int. Cl.[5] ............................................. C10L 1/18
[52] U.S. Cl. ........................................ 44/449; 568/697
[58] Field of Search ............... 44/77, 53, 56; 568/697

[56] References Cited

U.S. PATENT DOCUMENTS

| | | | |
|---|---|---|---|
| 3,849,082 | 11/1974 | Kozlowski et al. | 44/56 |
| 3,912,463 | 10/1975 | Kozlowski et al. | 44/56 |
| 3,979,461 | 9/1976 | Ancillotti et al. | 568/697 |
| 4,320,232 | 3/1982 | Volkamer et al. | 568/697 |
| 4,324,924 | 4/1982 | Torck et al. | 568/697 |
| 4,423,251 | 12/1983 | Piyado et al. | 568/697 |
| 4,503,264 | 3/1985 | Al-Muddarris et al. | 568/697 |
| 4,554,386 | 11/1985 | Groeneveld et al. | 568/697 |
| 4,554,386 | 11/1985 | Groeneveld et al. | 568/697 |
| 4,647,703 | 3/1987 | Torck et al. | 568/697 |
| 4,684,757 | 8/1987 | Avidan et al. | 585/331 |
| 4,714,787 | 12/1987 | Bell | 568/697 |

*Primary Examiner*—Margaret B. Medley
*Attorney, Agent, or Firm*—Alexander J. McKillop; Charles J. Speciale; L. G. Wise

[57] ABSTRACT

Isopentene, or isoamylene, conversion to methyl tert-amyl ether can be substantially improved while high conversion of isobutylene to methyl tert-butyl ether can be maintained by carrying out the overall etherification process with alkanol in a staged manner, wherein the first stage is methanol etherification of a $C_5+$, or $C_5$, hydrocarbon feedstream rich in isoamylene and the second stage is etherification to produce MTBE and additional TAME from a $C_4+$, or $C_4$, feedstream. Unreacted methanol and hydrocarbons from the first etherification are uniquely separated by fractionation from the TAME product by using the second stage $C_4+$ feedstream as a reflux stream to the fractionator and passed to the second etherification zone. Products from the second etherification zone are separated by distillation to produce MTBE, TAME and $C_5+$, or $C_5$, hydrocarbons as a bottom stream.

21 Claims, 1 Drawing Sheet

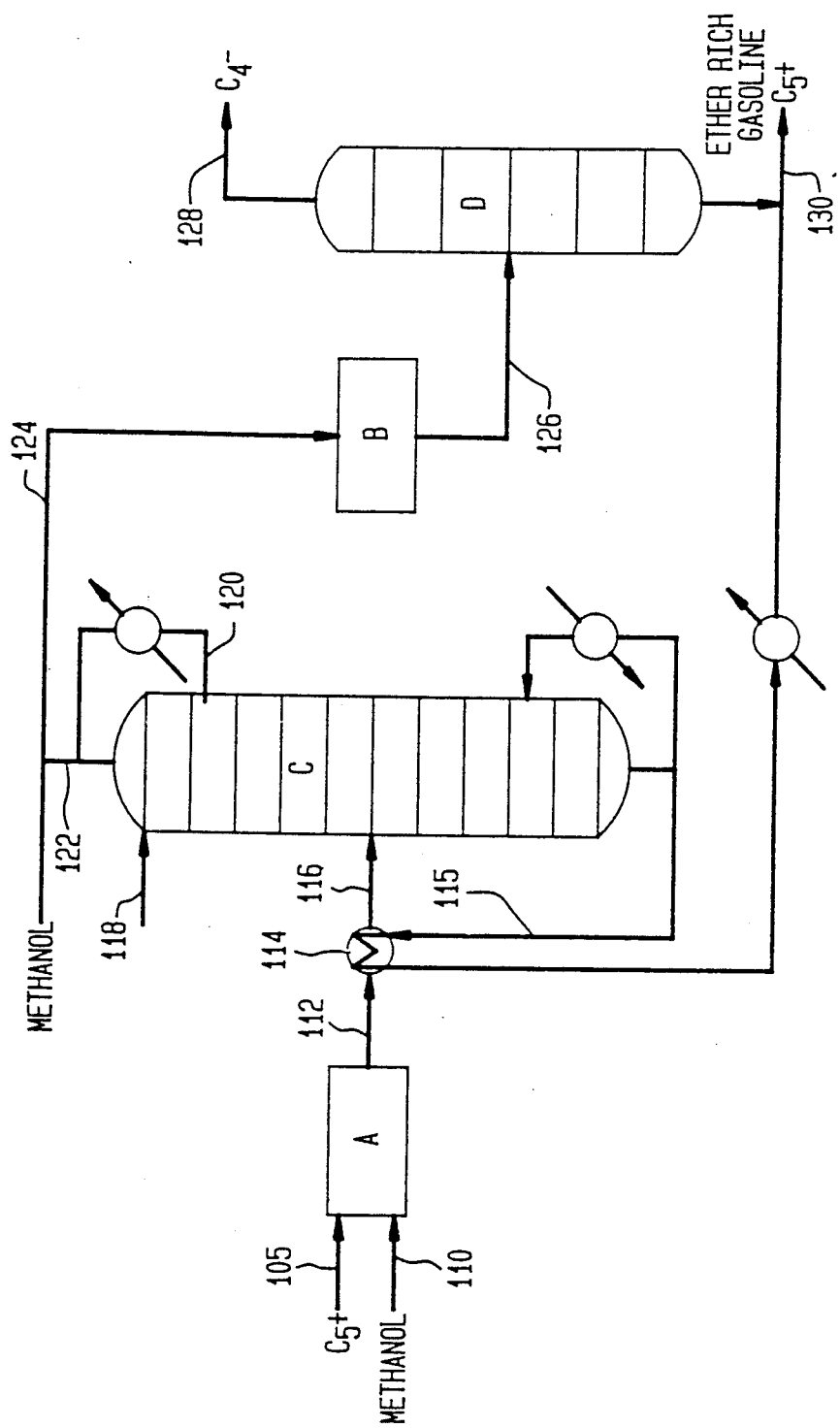

HIGH CONVERSION TAME AND MTBE PRODUCTION PROCESS

This invention relates to the production of high octane tertiary alkyl ethers and gasoline. In particular, the invention relates to the production of methyl tertiary butyl ether (MTBE) and methyl tertiary amyl ether (TAME) by a process which significantly improves the conversion of isoamylene to TAME and produces high octane gasoline.

BACKGROUND OF THE INVENTION

It is well known that isobutylene may be reacted with methanol over an acidic catalyst to provide methyl tertiary butyl ether (MTBE) and isoamylenes may be reacted with methanol over an acidic catalyst to produce tertiary amyl methyl ether (TAME). The reaction is a useful preparation for these valuable gasoline octane enhancers and is typical of the reaction of the addition of lower alkanol to the more reactive tertiary alkenes, or iso-olefins, of the type $R_2C=CH_2$ or $R_2C=CHR$ under mild conditions to form the corresponding tertiary alkyl ethers. The feedstock for the etherification reaction may be taken from a variety of refinery process streams such as the unsaturated gas plant of a fluidized bed catalytic cracking operation containing mixed light olefins, preferably rich in isobutylene and isopentenes or isoamylene.

Generally, it is known that asymetrical $C_5$-$C_7$ alkyl tertiary alkyl ethers are particularly useful as octane improvers for liquid fuels, especially gasoline. MTBE, ethyl t-butyl ether (ETBE), isopropyl t-butyl ether (IPTBE) and TAME are known to be high octane ethers. The article by J. D. Chase, et al., *Oil and Gas Journal*, Apr. 9, 1979, discusses the advantages one can achieve by using such materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114. Increasing demand for high octane gasolines blended with high octane ethers as octane boosters and supplementary fuels has created a significant demand for these ethers, especially MTBE and TAME.

In these etherification processes, a problem of major importance is the separation of methanol from the etherification reaction product due to the proclivity of methanol to form a very dilute azeotropic mixture with hydrocarbons and the strong solubility of methanol in both water and hydrocarbons. Due largely to these factors, the cost associated with methanol separation and recycling in the etherification reaction represents approximately 30% of the cost of the total etherification process. While it would be useful from an equilibrium standpoint to use large excesses of methanol in etherification, subsequent separation problems have limited that process improvement. Currently, preparation of MTBE and TAME is carried out using $C_4+$ hydrocarbon feedstock where methanol is present in the etherification step in about less than a three weight percent excess based on iso-olefins in the feed. This is effective in converting over ninety percent of isobutylene to MTBE, but isoamylene conversion is limited to about sixty-five percent under these conditions. Attempts to improve the conversion of isoamylene to TAME by manipulating the chemical equilibria with large excesses of methanol while maintaining high conversion of isobutylene to MTBE have proven disappointing, incurring heavy economic burdens on separation of the product.

Representative teachings in the prior art directed to the effort to improve the iso-olefin etherificaton process include U.S. Pat. No. 4,647,703 to Torck et al. which describes a multi-stage etherification process wherein effluent from the first stage is passed to a fractionator, a bottoms product containing ethers is withdrawn, and a top product containing unreacted light olefins and alcohol is passed to a second stage etherification reactor.

In U.S. Pat. No. 4,554,386 to Groeneveld et al. an iso-olefin etherification process is disclosed wherein multiple reactors are employed. An MTBE separation column is positioned after the first reactor.

In U.S. Pat. No. 4,324,924 to Torck et al. a multi-stage process is disclosed for preparing MTBE wherein effluent from the first stage is fractionated and the overhead is passed to a second stage for processing.

It is an object of the instant invention to provide a process for the production of MTBE and TAME that includes high conversion of isoamylene to TAME.

SUMMARY OF THE INVENTION

It has been discovered that the conversion of isopentene, or isoamylene, to methyl tert-amyl ether can be substantially improved while the typically high conversion of isobutylene to methyl tert-butyl ether can be maintained by carrying out the overall etherification process with alkanol such as methanol in a staged manner, wherein the first stage is methanol etherification of a $C_5+$, or $C_5$, hydrocarbon feedstream rich in isoamylene and the second stage is etherification to produce MTBE and additional TAME from a $C_4+$, or $C_4$, feedstream. In the first stage etherification, the methanol concentration or feed rate is maintained at an amount sufficient to assure that downstream fractionation of the reaction effluent produces low methanol carry-over and a TAME product with low methanol content. Unreacted methanol and hydrocarbons from the first etherification stage are uniquely separated by fractionation from the TAME product by using the second stage $C_4+$ feedstream as a reflux stream to the fractionator. The methanol-free added reflux stream provides additional hydrocarbon needed to separate methanol and enhance methanol flowrate in the fractionator overhead stream. With the addition of fresh methanol, as may be required, these streams are passed to the second etherification zone. Products from the second etherification zone are separated by distillation, preferably in a debutanizer, to produce MTBE, TAME and $C_5+$, or $C_5$, hydrocarbons as a bottom stream.

More particularly, the invention comprises a process for the production of high octane gasoline containing alkyl tertiary alkyl ethers which includes the steps of: contacting $C_5+$ hydrocarbon feedstream rich in isopentene and alkanol with acidic catalyst in a first etherification zone under isopentene etherification conditions; fractionating the effluent from the first zone in conjunction with an added $C_4+$ hydrocarbon reflux stream, whereby a fractionator bottom stream comprising alkyl tertiary amyl ether is produced and an overhead stream comprising unreacted alkanol and $C_4+$ hydrocarbon; introducing the overhead stream and fresh alkanol into a second etherification zone containing acidic catalyst under iso-olefin etherificaton conditions to produce an effluent stream comprising alkyl tertiary butyl ether, alkyl tertiary amyl ether, unreacted alkanol and $C_{4+}$ hydrocarbon; and separating the second zone effluent to produce a stream comprising $C_{5+}$ ether rich high octane gasoline and a stream containing unreacted alkanol and $C_{4-}$ hydrocarbon.

DESCRIPTION OF THE FIGURE

The figure is a schematic diagram of the process of the present invention.

DETAILED DESCRIPTION OF THE INVENTION

Typical hydrocarbon feedstock materials for etherification reactions include olefinic streams, such as FCC light cracked gas containing butene isomers, often in mixture with substantial amounts of propene, propane, n-butane and isobutane. The $C_4$ components usually contain a major amount of unsaturated compounds, such a 10-20% isobutylene, 30-50% linear butenes, and small amounts of butadiene. Also, $C_{4+}$ heavier olefinic hydrocarbon streams may be used, particularly mixtures of isobutylene and isoamylene. These aliphatic streams are produced in a variety of petroleum refinery operations such as catalytic cracking of gas oil or the like. $C_5$ and $C_{5+}$ hydrocarbon streams containing isoamylene may be obtained from similar sources by debutanization.

The reaction of methanol with isobutylene and isoamylenes at moderate conditions with a resin catalyst is known technology, as provided by R. W. Reynolds, et al., *The Oil and Gas Journal*, June 16, 1975, and S. Pecci and T. Floris, *Hydrocarbon Processing*, December 1977. An article entitled "MTBE and TAME—A Good Octane Boosting Combo," by J. D. Chase, et al., *The Oil and Gas Journal*, Apr. 9, 1979, pages 149-152, discusses the technology. A preferred catalyst is a sulfonated polystyrene resin or polymeric sulfonic acid exchange resin such as Amberlyst 15. Other acidic catalysts may be used. Acidic Zeolites, such as ZSM-5 and zeolite Beta, are particularly useful catalysts.

Processes for producing and recovering MTBE and other methyl tertiaryl alkyl ethers from $C_4$-$C_7$ iso-olefins are known to those skilled in the art, such as disclosed in U.S. Pat. Nos. 4,544,776 (Osterburg, et al.) and 4,603,225 (Colaianne et al.). In the prior art various suitable extraction and distillation techniques are known for recovering ether and hydrocarbon streams from etherification effluent.

In the present invention methanol is the preferred lower or light alkanol. However, other alkanols may be used. Lower alkyl or alkanol in the present invention refers to $C_1$-$C_4$ alkyl derived from etherification using methanol, ethanol, 1-propanol, isopropanol, 2-butanol and 1-butanol. Tertiary alkyl refers to $C_4$-$C_5$ tertiary alkyl groups derived from the etherification of iso-olefins such as isobutene and isoamylene.

Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt %.

Isobutylene and isoamylene etherification conditions are known in the art and, in the instant invention, comprise mild conditions of low temperature and high liquid hourly space velocity (LHSV). Etherification temperature can range from 20° C. to 105° C. and preferably between 60° and 125° C.; more preferably between 50°-70° C.

The process of the present invention produces alkyl tertiary alkyl ethers include methyl tertiary butyl ether, methyl tertiary amyl ether, ethyl tertiary butyl ether, ethyl tertiary amyl ether, isopropyl tertiary amyl ether and isopropyl tertiary butyl ether. In the preferred embodiments of this invention to produce high octane ethers, methanol is reacted in contact with acidic catalyst with $C_5$ or $C_{5+}$ olefinic hydrocarbon feedstock rich in isopentene to produce methyl tertiary amyl ether. Preferably, at least 50% more methanol leaves the first stage reactor than in a conventional TAME process which separates methanol from TAME using a fractionation tower. In the process unreacted methanol in the first stage effluent comprises between 0.1 and 100 weight percent, based on unreacted isoamylene therein. Preferably, unreacted methanol in the effluent comprises about 7-70 weight percent, based on isoamylene therein. As a consequence of carrying out the etherification in the absence of more reactive iso-olefins such as isobutylene and forcing the equilibrium toward the formation of ether by enhancing methanol flowrate or concentration, the conversion of isoamylene is substantially improved and production of TAME increased. However, the relatively high flow of unreacted methanol conventionally would end up in the TAME product as a result of the formation of a dilute, lower boiling azeotrope of methanol and $C_5$ hydrocarbon during fractionation. Typically, this would present problems of an aqueous phase formation in gasolines containing the product.

The present invention avoids the foregoing separation problems of relatively high flow of unreacted methanol by providing an olefinic $C_4$ or $C_{4+}$ feedstream to the TAME fractionator which is placed in an interstage configuration upstream of an MTBE/TAME etherification reactor. Preferably, the hydrocarbon stream is added in an upper portion of the fractionator as a tower reflux at a tower top temperature of about 38° C. and pressure of less than about 100 psig. With the added hydrocarbon reflux feedstream the formation of azeotrope and separation of unreacted methanol is readily accomplished. The tower overhead containing methanol and $C_{4+}$ hydrocarbons including isobutylene and isoamylene is utilized as the feedstream to a second etherification zone to form MTBE and additional TAME. Fresh methanol, as required, may also be fed to the second etherification zone. The effluent from the second zone is separated, preferably in a debutanizer, to provide $C_{5+}$ gasoline rich in MTBE and TAME as a bottom stream and an overhead stream containing unreacted methanol and $C_{4-}$ hydrocarbons.

Referring to the Figure, a schematic flow diagram depicts the process of the present invention. The diagram shows the following principal components for the novel process and reactor system: a TAME etherification reactor zone A, preferably containing an acidic zeolite catalyst; a reactor zone B, also containing acidic catalyst such as Amberlyst 15 from Rohm and Haas for etherification to produce MTBE and TAME; and fractionators C and D for the separation of the products from the etherification zones A and B, respectively. The reactor zones A and B may each contain several reactors connected in series through heat exchangers in order to control the etherification reaction exotherm. Generally, these reactor zones operate at temperatures between about 30° C. and 150° C. at moderate pressure.

A $C_5$ or $C_5+$ hydrocarbon feedstream 105 which is rich in isoamylene is passed to the etherification zone A together with a methanol feedstream 110. THe effluent 112 from reactor A, after heat exchange with the bottom stream 115 from the fractionator C is passed 116 to a mid-portion of the fractionator. The 112 effluent comprises TAME, unreacted methanol and $C_5$ to $C_5+$ hydrocarbons. A $C_4$ or $C_4+$ stream 118 containing isobutylene is introduced into a top portion of the fractionator C, forming at least a component of the fractionator reflux stream 120 comprising $C_5-$ hydrocarbons and methanol. The quantity of the added reflux stream is sufficient, when combined with $C_5-$ hydrocarbons contained in the 112 effluent, to assure the separation of unreacted methanol in the 112 stream into the overhead stream 122. The 115 bottom stream from the fractionator comprises $C_5+$ products containing TAME. When the 105 feedstream is $C_5+$, higher gasoline boiling range products are included in the 115 fractionator bottom stream. The overhead stream 122, now containing $C_4+$ hydrocarbons and methanol is passed to reactor B, preferably in conjunction with added methanol feedstream 124 to make up a slight excess, about 1 weight percent, of methanol in the reactor compared to iso-olefins. The etherification effluent from the B reactor contains MTBE, TAME, unreacted methanol and $C_4+$ hydrocarbons and is passed 126 to a mid-portion of debutanizer D for separation into an overhead stream 128 comprising methanol and $C_4-$ hydrocarbons and a bottom product stream 130 of ether rich $C_5+$ gasoline.

While the instant invention has been described by specific examples and embodiments, there is no intent to limit the inventive concept except as set forth in the following claims.

What is claimed is:

1. A process for the production of methyl tertiary butyl ether and methyl tertiary amyl ether in high yield, comprising:
    contacting methanol and a feedstream comprising $C_5$ hydrocarbon rich in isoamylene with acidic etherification catalyst in a first etherification zone under isoamylene etherification conditions;
    separating effluent from said first etherification zone to produce a stream comprising unreacted methanol and $C_5$ hydrocarbon and a product stream comprising methyl tertiary amyl ether;
    introducing said unreacted methanol and hydrocarbon stream, fresh methanol and a feedstream comprising $C_4$ hydrocarbon rich in isobutylene into a second etherification zone under iso-olefins etherification conditions in contact with acidic etherification catalyst;
    separating effluent from said second etherification zone to produce a stream comprising unreacted methanol and $C_4$ hydrocarbons and a product stream comprising methyl tertiary butyl ether and methyl tertiary amyl ether.

2. The process of claim 1 wherein said first zone effluent is separated in a fractionator, wherein said second zone $C_4$ feedstream is introduced to said fractionator to enhance the separation of unreacted methanol.

3. The process of claim 2 wherein a portion of said $C_4$ feedstream is introduced to a top portion of said fractionator as a reflux stream.

4. The process of claim 1 wherein said $C_5$ and $C_4$ hydrocarbon feedstreams independently comprise $C_5+$ or $C_4+$ hydrocarbon whereby said second zone product stream comprises $C_5+$ high octane gasoline containing methyl tertiary butyl ether and methyl tertiary amyl ether.

5. The process of claim 1 wherein the feedstreams to said second zone comprise essentially said first zone unreacted methanol and hydrocarbon stream and said $C_4$ feedstream.

6. The process of claim 2 wherein said unreacted methanol comprises between 0.1 and 100 weight percent, based on unreacted isoamylene.

7. The process of claim 6 wherein said methanol comprises about 20 weight percent.

8. The process of claim 1 wherein said acidic catalyst includes acidic zeolites and acidic resins.

9. The process of claim 8 wherein said catalyst includes ZSM-5, Zeolite Beta and sulfonated polystyrene resins.

10. The process of claim 1 wherein said isoamylene etherification conditions comprise temperature between 30° and 150° C.

11. The process of claim 1 wherein said iso-olefins etherification conditions comprise temperature of about 50°–70° C.

12. A process for the production of high octane gasoline containing alkyl tertiaryl alkyl ethers, comprising:
    contacting $C_5+$ hydrocarbon feedstream rich in isopentene and alkanol with acidic catalyst in a first etherification zone under isopentene etherification conditions;
    fractionating effluent from said first zone in conjunction with added $C_4+$ hydrocarbon stream, whereby a fractionator bottom stream comprising alkyl tertiary amyl ether is produced an overhead stream comprising unreacted alkanol and $C_4+$ hydrocarbon;
    introducing said overhead stream and fresh alkanol into second etherification zone containing acidic catalyst under iso-olefin etherification conditions to produce an effluent stream comprising alkyl tertiary butyl ether, alkyl tertiary amyl ether, unreacted alkanol and $C_4+$ hydrocarbon;
    separating said second zone effluent to produce a stream comprising $C_5+$ ether rich high octane gasoline and a stream containing unreacted alkanol and $C_4-$ hydrocarbon.

13. The process of claim 12 wherein said alkanol includes $C_1-C_4$ alkanol.

14. The process of claim 13 wherein said alkanol comprises methanol.

15. The process of claim 12 wherein said alkyl tertiary alkyl ethers include methyl tertiary butyl ether, methyl tertiary amyl ether, ethyl tertiary butyl ether, ethyl tertiary amyl ether, isopropyl tertiary amyl ether and isopropyl tertiary butyl ether.

16. The process of claim 12 wherein said unreacted alkanol comprises between 0.1 and 100 weight percent, based on unreacted isopentene.

17. The process of claim 16 wherein said alkanol comprises about 20 weight percent.

18. The process of claim 12 wherein said acidic catalyst includes acidic zeolites and acidic resins.

19. The process of claim 18 wherein said catalyst includes ZSM-5, zeolite Beta and sulfonated polystyrene resins.

20. The process of claim 12 wherein said second zone effluent is separated in a debutanizer.

21. The process of claim 12 wherein said first zone effluent is fractionated in conjunction with added $C_3+$ hydrocarbon.

* * * * *